(12) United States Patent
Higashi et al.

(10) Patent No.: US 10,292,845 B2
(45) Date of Patent: May 21, 2019

(54) STENT, METHOD FOR PRODUCING SAME AND DEVICE FOR PRODUCING SAME

(71) Applicant: KANEKA CORPORATION, Osaka-shi, Osaka (JP)

(72) Inventors: Ryogo Higashi, Settsu (JP); Tamotsu Shimada, Settsu (JP)

(73) Assignee: KANEKA CORPORATION, Osaka-Shi (JP)

( * ) Notice: Subject to any disclaimer, the term of this patent is extended or adjusted under 35 U.S.C. 154(b) by 0 days.

(21) Appl. No.: 14/889,654

(22) PCT Filed: Apr. 25, 2014

(86) PCT No.: PCT/JP2014/061728
§ 371 (c)(1),
(2) Date: Nov. 6, 2015

(87) PCT Pub. No.: WO2014/181713
PCT Pub. Date: Nov. 13, 2014

(65) Prior Publication Data
US 2016/0120671 A1    May 5, 2016

(30) Foreign Application Priority Data
May 7, 2013   (JP) .................. 2013-097710

(51) Int. Cl.
*A61F 2/90* (2013.01)
*A61F 2/915* (2013.01)

(52) U.S. Cl.
CPC ............. *A61F 2/90* (2013.01); *A61F 2/915* (2013.01); *A61F 2220/0033* (2013.01);
(Continued)

(58) Field of Classification Search
CPC .............................................. A61F 2250/0098
See application file for complete search history.

(56) References Cited

U.S. PATENT DOCUMENTS

| 5,725,572 A | 3/1998 | Lam et al. |
| 6,022,374 A | 2/2000 | Imran |

(Continued)

FOREIGN PATENT DOCUMENTS

| JP | 8-126704 A | 5/1996 |
| JP | 2003-517872 A | 6/2003 |

(Continued)

OTHER PUBLICATIONS

International Search Report, issued in PCT/JP2014/061728, dated Jun. 3, 2014.

*Primary Examiner* — Jacqueline Woznicki
(74) *Attorney, Agent, or Firm* — Birch, Stewart, Kolasch & Birch, LLP (57) ABSTRACT

According to a method for producing a stent which is formed into a tubular body and includes at least one marker formed from a marker housing and a marker insert including: using an indenter having a partially spherical shaped distal end, the distal end coming into contact with the marker insert when the marker insert is pressed with the indenter and is pressure fitted to an opening provided on the marker housing to fix it thereon, a sufficient load can be applied to a radiopaque marker insert when the marker insert is attached to the stent, and further a stent having a radiopaque marker whose marker housing has little damage can be produced.

9 Claims, 6 Drawing Sheets

US 10,292,845 B2

Page 2

(52) U.S. Cl.
CPC . *A61F 2230/0069* (2013.01); *A61F 2240/002* (2013.01); *A61F 2250/0096* (2013.01); *A61F 2250/0098* (2013.01)

(56) References Cited

U.S. PATENT DOCUMENTS

| | | |
|---|---|---|
| 6,334,871 B1 | 1/2002 | Dor et al. |
| 6,554,854 B1 | 4/2003 | Flanagan |
| 2004/0088039 A1 | 5/2004 | Lee et al. |
| 2004/0236409 A1 | 11/2004 | Pelton et al. |
| 2005/0085896 A1 | 4/2005 | Bonsignore et al. |
| 2007/0156230 A1 | 7/2007 | Dugan et al. |
| 2007/0266542 A1* | 11/2007 | Melsheimer .............. A61F 2/91 29/522.1 |
| 2008/0288046 A1 | 11/2008 | Hemerick et al. |

FOREIGN PATENT DOCUMENTS

| | | |
|---|---|---|
| JP | 2004-358242 A | 12/2004 |
| JP | 2005-118571 A | 5/2005 |
| JP | 2009-522050 A | 6/2009 |

* cited by examiner

PRIOR ART

STENT, METHOD FOR PRODUCING SAME AND DEVICE FOR PRODUCING SAME

TECHNICAL FIELD

The present invention relates to a stent for indwelling in a living body, a method for producing the same, and a device for producing the same. In particular, the present invention relates to a stent having a radiopaque marker, a method for producing the same, and a device for producing the same.

BACKGROUND ART

A stent is generally a medical device for treating various diseases caused by stenosis or occlusion of a blood vessel or another in vivo lumen. The stent is a medical device, which has, for example, an expandable mesh structure part, expands a lesion site such as a stenosis or occlusion site from the inside, and is indwelled in the lesion site to maintain an inside diameter of a lumen with the lesion.

The stent is used in a living body, and thus once the stent is inserted into the body, the position thereof cannot be visually confirmed. In usual, accordingly, markers including a radiopaque material (hereinafter referred to as marker inserts) are provided on pre-determined positions on the stent, and a medical treatment is advanced while exact positions of the markers are confirmed under an X-ray illumination.

A method in which marker inserts are pressure fitted to an opening of a marker housing provided on a stent (Patent Document 1 and Patent Document 2); a method in which marker inserts are welded to a stent using a laser (Patent Document 3), or a method in which marker inserts are formed in a structural element of a stent by using a plating method (Patent Document 4), or the like has been proposed as a method for attaching the marker inserts to the stent. Of these, the method in which the marker inserts are pressure fitted to the opening of the marker housing is preferably used, because it is a simple method requiring no particular, special facilities or techniques, and less galvanic corrosion occurs.

CITATION LIST

Patent Literatures

Patent Document 1: JP-T No. 2009-522050
Patent Document 2: JP-A No. 2004-358242
Patent Document 3: JP-A No. H08-126704
Patent Document 4: JP-T No. 2003-517872

SUMMARY OF INVENTION

Technical Problem

When the marker insert is attached to the marker housing on the stent by pressure fitting, it is necessary to fit the marker insert to the housing with application of a sufficient pressure when it is attached, in order to prevent falling away of the marker insert from the stent during the use of the stent. At that time, however, the pushing load is applied not only to the marker insert but also to the marker housing and, sometimes, a mesh structure part of the stent, and thus problems arises such as generation of cracks on the marker housing on the stent due to stress of the stent to the marker housing at the time of pressurization, or occurrence of damage of the marker housing, i.e., the broken marker housing.

In order to solve the problems described above, the present invention aim at providing a method and a device for producing a stent, according to which a sufficient load can be applied to a radiopaque marker insert when a marker insert is attached to the stent, and a stent having a less damaged marker housing can be provided.

Solution to Problem

As a result of the present inventors' painstaking studies for solving the problems described above, the present invention has been completed. A method for producing a stent of the present invention is, accordingly, a method for producing a stent which is formed into a tube and includes at least one marker including a marker housing and a marker insert including: using an indenter having a partially spherical shaped distal end, the distal end coming into contact with the marker insert when the marker insert is pressed with the indenter and is pressure fitted to an opening provided on the marker housing to fix it thereon.

It is preferable that the indenter in the production method of the present invention is formed of a proximal region and a distal end, the proximal region having a circular cross-sectional shape whose outside diameter is equal to or larger than an inside diameter of the opening of the marker housing.

It is preferable that the distal end of the indenter in the production method of the present invention has a radius of curvature equal to or larger than a radius of the opening of the marker housing.

A device for producing a stent of the present invention is a device for producing a stent which is formed into a tube and includes at least one marker including a marker housing and a marker insert including: a press apparatus equipped with an indenter of pressing the marker insert and pressure fitting it to an opening provided on the marker housing; a microscope; and a mandrel, wherein a distal end, of the indenter, coming into contact with the marker insert has a partially spherical shape.

It is preferable in the device for producing the stent of the present invention that the mandrel can move relatively to the press apparatus and the microscope so that a pre-determined position of the mandrel is consistent with a central axis of the indenter and a center of a visual field of the microscope.

A stent of the present invention is a stent which is formed into a tube and includes at least one marker including a marker housing and a marker insert, wherein the marker insert has a recessed partially spherical outer surface shape.

It is preferable in the stent of the present invention that a position of an outer surface of the marker insert is consistent with a position of an outer surface of the marker housing at a boundary between the marker insert and the marker housing.

Advantageous Effects of Invention

According to the production method and the production device, a marker insert can be easily attached to a marker housing of a stent, and further a large load can be applied to the marker insert without generation of cracks on or occurrence breakage of the marker housing of the stent to pressure fit the marker insert, and thus a stent, which causes less falling away of the marker insert when it is used, can be produced.

BRIEF DESCRIPTION OF THE DRAWINGS

FIG. 1 (a) is a development view of a stent provided with a marker. FIG. 1 (b) is a cross-sectional view at a line I-I in FIG. 1(a).

DESCRIPTION OF EMBODIMENTS

One embodiment of a method for producing a stent according to the present invention will be explained in detailed below, referring to the drawings, but the present invention is not limited thereto.

(Stent)

A stent which can be used in the present invention may include, for example, (a) a coil type including one linear metal or polymeric material; (b) a type processed by cutting a metal tube with a laser; (c) a type assembled by welding linear members with a laser; and (d) a type produced by weaving plural linear metals, and a stent can be appropriately selected from the stents described above depending on the objective. Among the stents described above, a stent having a tubular shape and a mesh structure part is preferable. A cylindrical shape is preferable among the tubular stents.

A stent is usually used in a state in which the stent is attached to a catheter (a delivery system: a delivery device) having a site in which a stent is installed, in order to deliver the stent to a lesion site. The stent can be generally classified into (A) a balloon expansion type in which the stent is mounted on an outer surface of a balloon, is delivered to a lesion site, and is expanded by the balloon at the lesion site; and (B) self-expansion type in which the stent is delivered to a lesion site with a catheter having a sheath member, which inhibits expansion, and is expands for itself at a lesion site by removing the member which inhibits the expansion, in terms of an expansion mechanism.

Either of the types (A) and (B) can be applied to the stent of the present invention, and the self-expansion type stent (hereinafter referred to as a self-expandable stent) is particularly preferably used in plastic operations of a urinary duct, a bile duct, or a peripheral artery.

Hereinafter explanations will be made taking the self-expandable stent as an example, but the present invention is not limited thereto.

Figure 1:
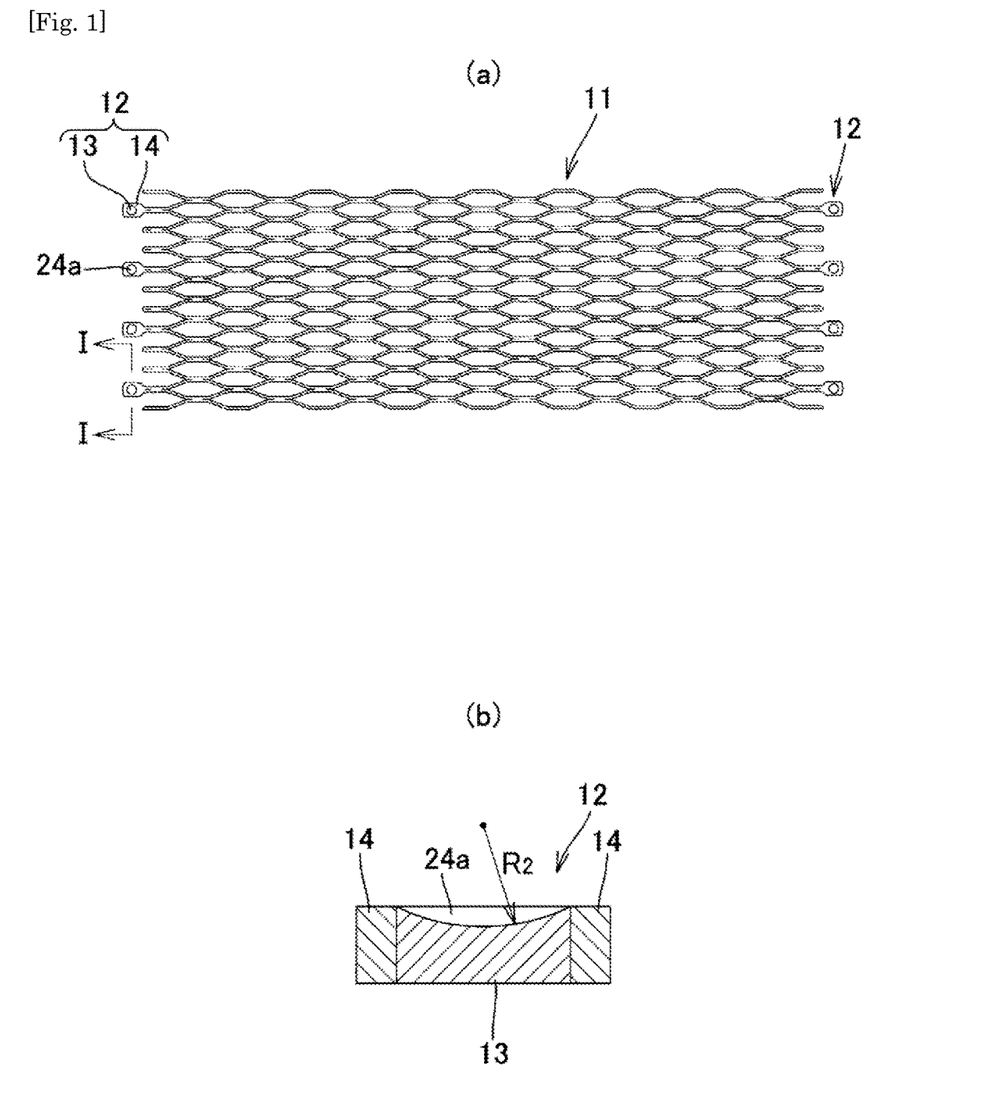

FIG. 1 (a) shows a whole development view of a tubular stent having a mesh structure part in an expanded state; and FIG. 1 (b) shows a cross-sectional view at a line I-I in FIG. 1(a). A tubular body formed in a state of continuing from an upper end to a bottom end in FIG. 1 (a) corresponds to the stent, which is not depicted in the drawing. The tubular body continues from one end to the other end thereof, has a hollow part surrounded by a mesh structure part, and opens at the both ends thereof. Hereinafter, a direction directed from one end to the other end along the hollow part (a crosswise direction in FIG. 1 (a)) is called as a major axis direction of a stent, and a direction crossing the major axis direction at right angles is called as a minor axis direction. FIG. 1 (a) is the development view of the stent, but, hereinafter, a number 11 in FIG. 1 (a) is applied to the stent which is formed into a tubular body, for convenience. A stent 11 having a mesh structure with a cylindrical shape is taken as an example.

As shown in FIG. 1 (a), the stent 11 includes radiopaque markers (hereinafter referred to as markers) 12 at the both ends thereof in the major axis direction. In the present invention, the marker refers to a part in which a marker insert 13 and a marker housing 14 are integrated. As shown in FIG. 1 (b), an outer surface 24a of the marker insert 13 has a recessed partially spherical shape. In a case where the surface shape is the recessed partially spherical shape as above, when the marker insert 13 is pressure fitted to an opening 26 by using an indenter to fix the insert, as described below, a stress caused by the indenter is uniformly dispersed, a residual stress in the marker insert 13 is reduced, and it is difficult to break the marker insert 13 after the fixing. In addition, it is possible to reduce an amount of the marker insert used compared to a case where a shape which is not the recessed shape is used.

The outer surface of the marker insert refers to an outer surface of the stent, i.e., a surface opposite to the hollow part of the tubular body. When the stent is inserted into an in vivo lumen and is indwelled therein, the outer surface of the marker insert is a surface coming into contact with an inner wall surface of the in vivo lumen.

The partially spherical shape of the recessed partially spherical surface is not particularly limited, and a radius of curvature $R_2$ thereof may be fixed or may vary. As described below, the radius of curvature $R_2$ corresponds to a part coming into contact with the marker insert 13 of partially spherical shape of a distal end of an indenter described below. The radius of curvature $R_2$ of the recessed partially spherical shape forming the outer surface 24a of the marker insert 13 is, accordingly, almost consistent with a radius of curvature $R_1$ of a distal end 27 of an indenter 21 described below.

Further, recesses and projections may be formed on the outer surface of the marker insert so long as the marker insert has substantially a recessed partially spherical shape.

A material used for the stent 11 is not particularly limited so long as it can endure during deformation such as expansion and diameter reduction, and indwelling. 316 L stainless steel, which is a stainless steel for medical use, tantalum, Co—Cr (cobalt-chromium) alloy, or Ni—Ti (nickel-titanium) alloy can be preferably used. In particular, the nickel-titanium alloy is more preferably used, because it has a shape memory property, a superelasticity, and an excellent processability, and it is easy to prevent the falling away of the marker insert by clamping it after press, when the marker housing is integrally formed. Of the nickel-titanium alloies, in particular, nickel-titanium alloy having about 50% to about 60% of nickel can be even more preferably used.

It is preferable that the stent 11 is designed so as to have the superelasticity at a body temperature, and to have an Af temperature (Austenite transformation finish temperature) of about 23 degree Celsius to about 37 degree Celsius.

A material which is used for the marker insert 13 is not particularly limited so long as it can have sufficient visibility in X-ray illumination. It is preferable to form it from a detectable substance such as an X-ray detectable substance or an ultrasonic detectable substance, and examples thereof may include metals such as gold, platinum, tungsten, tantalum, iridium, and palladium, and alloies thereof. In particular, tantalum, gold-palladium alloy, platinum-iridium alloy, Ni—Ti—Pd alloy, Ni—Ti—Au alloy, and the like are preferable, because it is easy to process them to a desirable shape. When the Ni—Ti alloy is used for the marker housing or the stent, tantalum is more preferable, whose ionization series is near to that of the nickel-titanium and which has a high molding processability, in order to prevent the galvanic corrosion. The marker insert 13 may be formed of the material described above alone, a mixed materials of two or more kinds thereof, or a mixed material thereof with another material for improving the strength and the processability.

A laser processing, an electrodischarge machining process, a mechanically cutting method, or an etching method can be preferably used as a method for molding the mesh structure part of the stent 11.

In addition, a tubular material may be molding formed, or it is possible that a planar sheet material is processed into a mesh, and then it is rolled and welded to form a tube.

In the present invention, a method in which a tubular material is cut into a cell shape by a laser processing to prepare a mesh shape can be preferably used.

The marker housing 14 may be integrally formed with the mesh structure part of the stent, or can be formed by attaching a separated member, which has been previously formed, to the mesh structure part. The method of integrally forming the marker housing 14 with the mesh structure part may include, for example, forming methods using an electrodischarge machining method, a chemical dissolution method, or the like when the mesh shape is formed, in addition to the laser processing described above.

The same material as used in the stent 11 described above can be used as a material which is used for the marker housing 14. When the marker housing is formed on the stent as the separated member, the material thereof may be the same as or different from the material for the stent.

In the present invention, the marker 12 is formed, for example, by inserting and joining the marker insert 13 to the opening (slot) 26 provided on the marker housing 14 connected to the both ends of the mesh structure part of the stent 11.

Although a state in which the marker insert 13 is installed in the slot 26 is not particularly limited, it is preferable that the position of the outer surface 24a of the marker insert 13 is consistent with the position of the outer surface 25 of the marker housing 14 at the boundary between the marker insert 13 and the marker housing 14. This eliminates a projection of the marker insert 13 from the outer surface of the stent, and allows the outer surface 25 of the marker housing 14 to be smoothly connected to the recessed partially spherical outer surface 24a of the marker insert 13. When there is no projection of the marker insert 13 as above, it is difficult for the marker insert 13 to catch a sheath member and the like in a delivery system when the stent is housed or released, thus resulting in prevention of falling away of the marker insert 13 from the slot 26. In addition, because the recessed partially spherical outer surface 24a of the marker insert 13 is smoothly continued from the outer surface 25 of the marker housing 14, an area of the marker 12 which comes into contact with the inner wall surface of the in vivo lumen can be decreased to reduce invasiveness.

Furthermore, it is more preferable that, as shown in FIG. 1 (b), the position of the outer surface 24a on the edge of the recessed partially spherical marker insert 13 is consistent with the position of the outer surface 25 of the marker housing 14, from the points described above.

Although the position on which the marker is installed is not particularly limited so long as the position of the stent can be confirmed under an X-ray illumination during an operation, it is preferable to install it on one edge in a major axis direction of the stent, for example, a proximal end or a distal end, because the indwelling position of the stent in a blood vessel can be preciously confirmed, and it is more preferable that, as shown in FIG. 1 (a), multiple markers are installed on both the proximal end and the distal end of the stent 11, because the expanded state thereof can be easily confirmed at the indwelling position of the stent. In particular, it is preferable that at least 4 markers 12 are provided at the edge of the stent 11, because an operator can easily confirm the expanded state of the stent 11 from various angles.

The marker 12 is preferably installed so as to form a substantial solid line clearly defining the edge of the stent 11 in a stent delivery system including a stent and a sheath under an X-ray illumination. When the stent 11 is released from the stent delivery system, the markers 12 are separated from each other and they form a flower shape as the stent 11 expands, and thus an operator can confirm that the stent 11 has been completely released from the stent delivery system and has been indwelled.

The phrase "to form a substantial solid line" refers to a state in which each marker is arranged on the same circumference. It means, for example, that the markers are arranged so that the adjacent markers are close to each other in a state in which the diameter of the stent 11 is reduced in the stent delivery system, and a line connecting the markers can be observed as a substantial solid line under an X-ray illumination. Such an arrangement of the markers can more clarify the position of the stent 11.

(Production Method of Stent)

FIG. 2 to FIG. 5 are a perspective view and cross-sectional views of one embodiment in the production method of the present invention.

Figure 2:
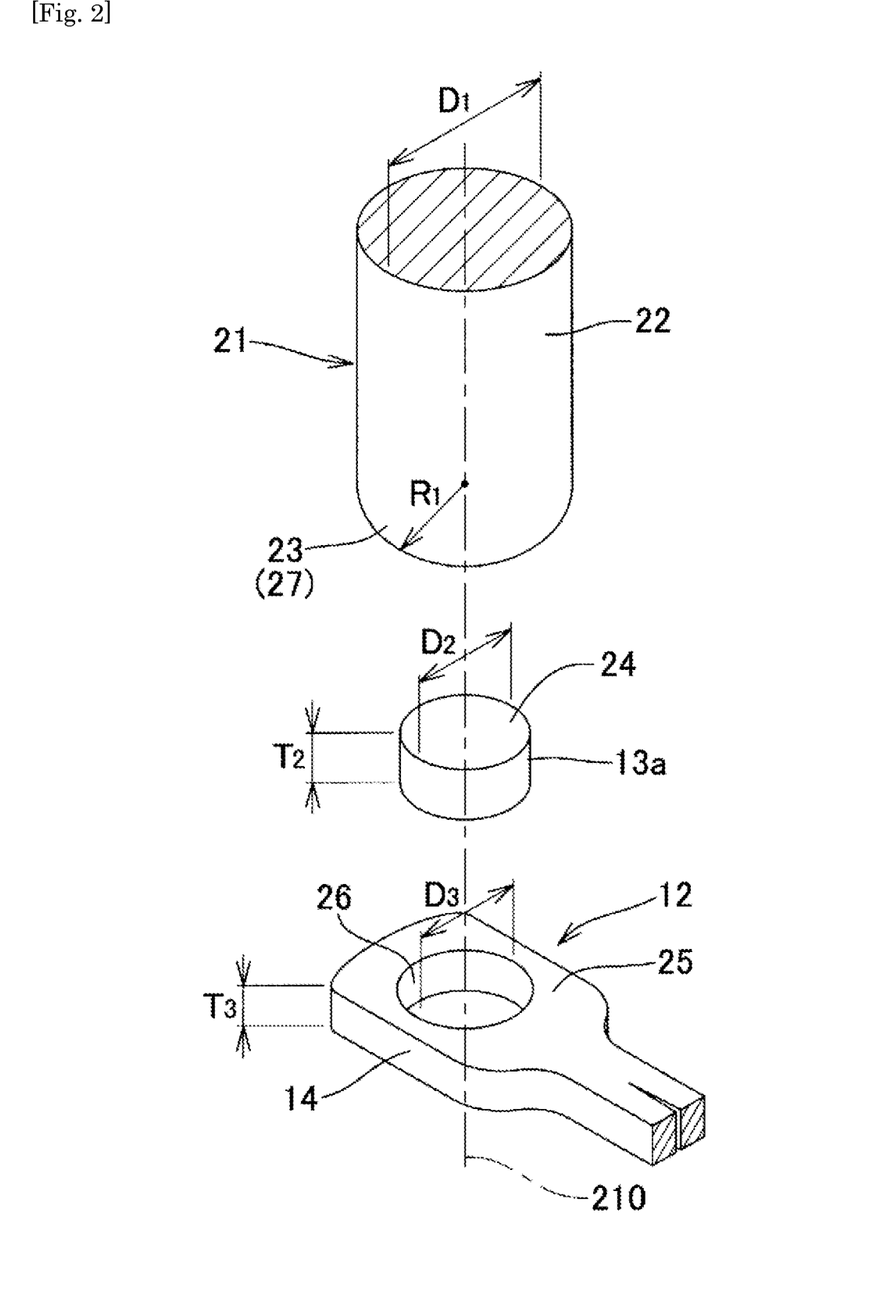
FIG. 2 is a perspective view showing a method of attaching a marker insert in the present invention.
Figure 3:
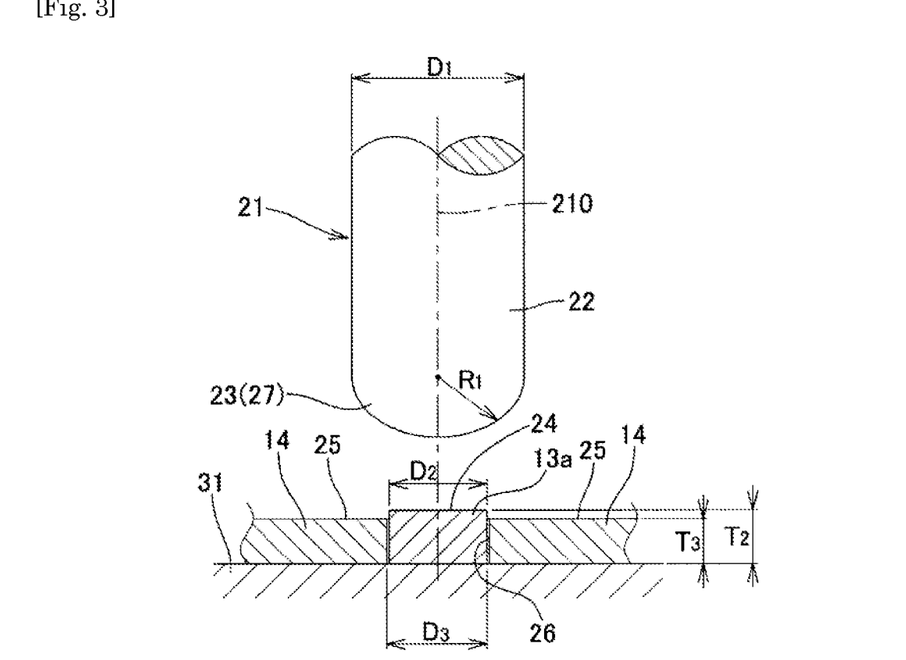
FIG. 3 is a cross-sectional view showing a state before a marker insert is attached in the present invention.

First, as shown in FIG. 2 and FIG. 3, a marker insert 13a, which has not been pressed yet, is inserted into an opening 26 of a marker housing 14 and is installed thereon. As shown in FIG. 2, in the present embodiment, the marker insert 13a, which has not been pressed yet, has a cylindrical shape, and the marker housing 14 has the opening 26, which is a columnar through hole. As shown in FIGS. 2 and 3, in the present embodiment, an indenter 21 has an central axis 210, parallel to a moving direction when the marker insert 13a, which has not been pressed yet, is pressed, and is formed of a proximal region 22 and a distal end 27, which are connected to each other in a direction of the central axis 210, the distal end 27 having a partially spherical shape. Note that in the following explanation, the spherically shaped distal end 27 is changed into a number 23, which is referred to as a partially spherical tip shape. Then, the marker insert 13 can be pressure fitted to the opening 26, provided on a marker housing 14, to fix the insert on the opening, using an indenter 21 having the partially spherical tip shape 23 with a radius of curvature of $R_1$ on the proximal region 22. As shown in FIG. 3, the marker insert 13a, which has not been pressed yet, is supported by a mandrel 31, which is arranged on a side opposite to a side on which the indenter 21 is arranged in relation to the marker housing 14. The mandrel 31 receives the pressure from the indenter 21 during the press working, and can help a desirable deformation of the marker insert 13a. This is more preferable in a case where the opening 26 is a through hole.

Figure 4:
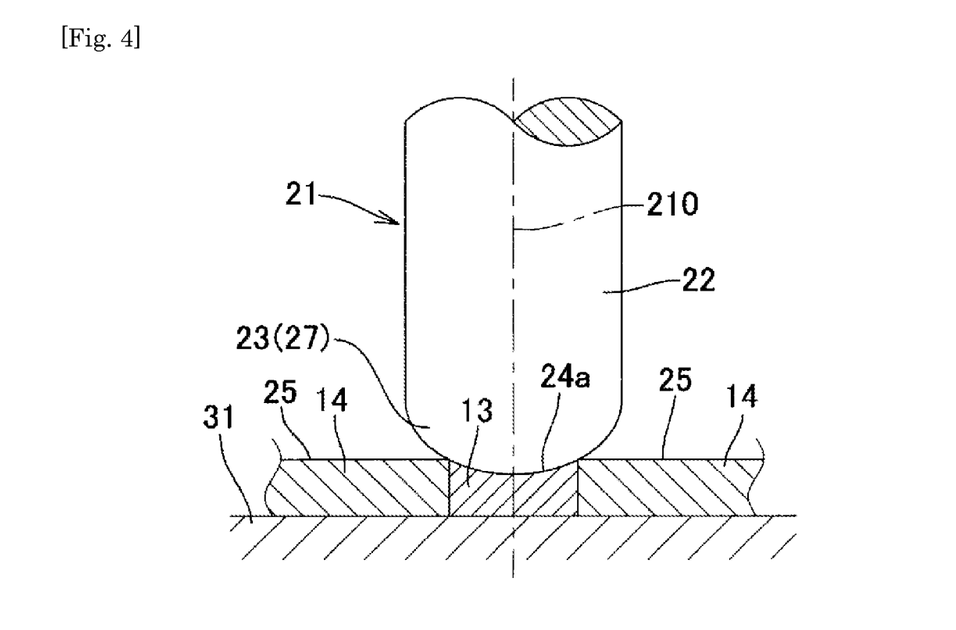
FIG. 4 is a cross-sectional view showing a state at the time when a marker insert is attached in the present invention.
Figure 6:
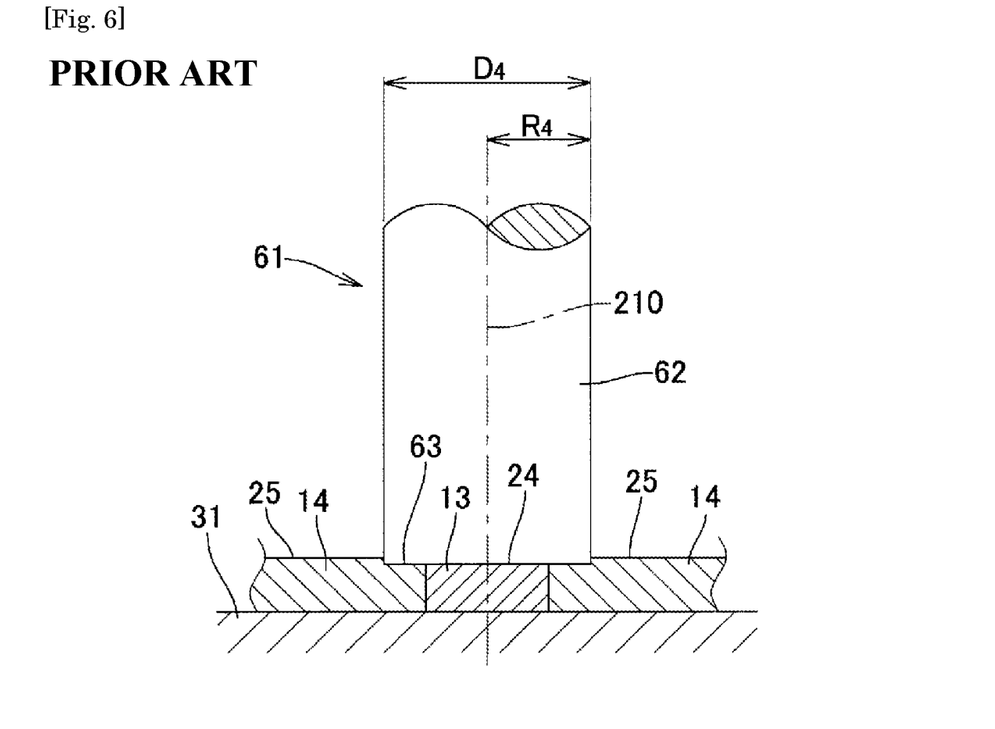
FIG. 6 is a cross-sectional view showing a state at the time when a conventional, general marker insert is attached.

As shown in FIG. 4, the columnar marker insert 13a, which has not been pressed yet, is deformed during the press working, i.e., it is expanded while it is brought into contact with a lumen surface 26a of the opening 26, thereby forming into a marker insert 13 whose outer surface is a recessed partially spherical shape. The distal end of the indenter 21 having the partially spherical tip shape is formed into a shape in which the distal end is substantially brought into contact only with the marker insert 13, and is not brought into contact with the outer surface 25 of the marker housing 14 during the press working. As described above, in the present invention, an area coming into contact with the marker insert 13 in the distal end of the indenter 21 has a partially spherical shape, and thus it is possible that the marker inserts 13a are sequentially pressed and deformed radially from the center of a pressing surface, when the distal end of the indenter 21 presses the marker insert 13a, which has not been pressed yet, to deform it. The distal end of the indenter 21, accordingly, pushes the marker insert more deeply from the outer surface 25 of the marker housing 14 toward the center of the outer surface 24 of the marker insert 13a; whereas, the depth at the edge 15 of the outer surface 24 of the marker insert 13a can be stopped at almost the same height of the outer surface 25. The marker insert 13a, accordingly, can be more effectively deformed by the press than a case of using a conventional indenter 61, for example as shown in FIG. 6 described below, thereby more securely holding the marker insert 13 in the opening 26 of the marker housing 14, and, at the same time, the distal end of the indenter 21 does not come into contact with the outer surface 25 of the marker housing 14. How far the marker insert moves in a direction of the central axis 210 of the indenter 21 when the indenter 21 presses the marker insert 13a, which has not been pressed yet, can be controlled considering properties of the material for the marker insert, a size of the marker insert 13a, which has not been pressed yet, a relationship in a size with the opening 26 of the marker insert 13a, and the like. The control factors may include, for example, a moving distance of the indenter 21, a press load when the indenter 21 presses the marker insert, a loading time of the press load, a moving speed, and the like. Of these, as for the control of the moving distance of the indenter, it is possible to move the indenter to a given position, but it is difficult to always attain the same press working, because the marker housing and the marker insert have actually a tolerance in the size. It is desired that the loading time of the press load is shortened as much as possible, because if the loading time is too long, then a lead time of the operation is prolonged, but in that situation, it is difficult to obtain a good marker holding strength. When the moving speed is too slow, the lead time of the operation is prolonged, and thus the moving speed is desirably made as fast as possible, but in that situation, it is difficult to control the press state. On the other hand, it is preferable to control the press load, because when the press load is controlled, then the marker insert can be always pushed until a load reaches a given value, and thus the same pressing work can be always attained. According to the effects of the present invention, when the press load is controlled, the good marker appearance and the holding strength can be attained without generation of cracks, appearing in Comparative Example 3, even if a large press load such as 200 N as shown in Example 3 described below, for example, is applied.

As described above, when the indenter 21 whose distal end, which comes into contact with the marker insert 13, has the partially spherical shape is used, the marker insert 13, obtained by applying the load to the columnar marker insert 13a, which has not been pressed yet, to deform it, can be pressure fitted to the opening 26, without occurrence of substantial deformation of the outer surface 25 of the marker housing 14, or distortion or breakage of the mesh structure part of the stent.

Figure 5:
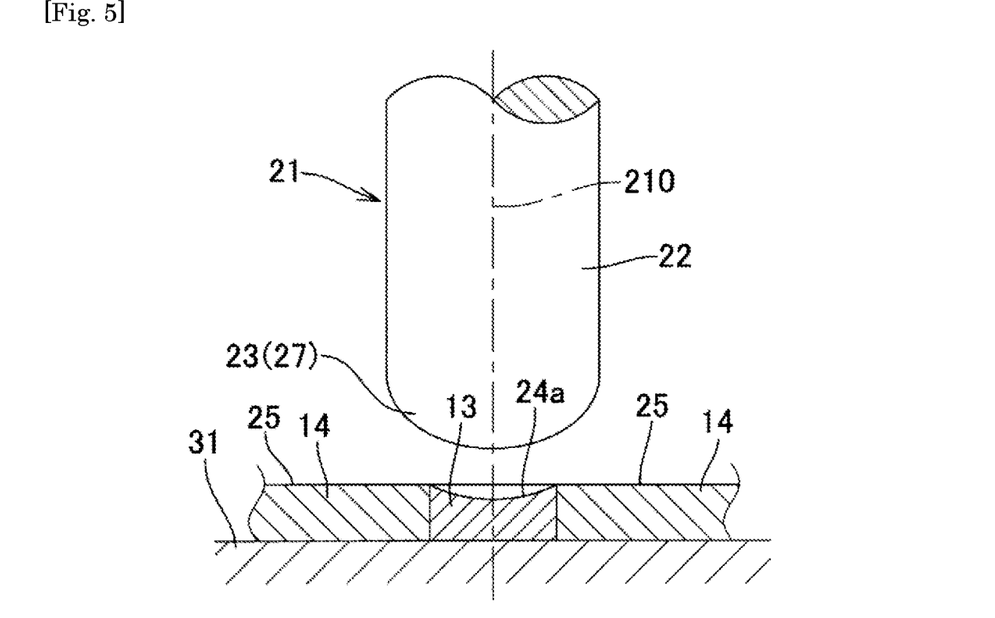
FIG. 5 is a cross-sectional view showing a state after a marker insert is attached in the present invention.

As shown in FIG. 5, the marker insert 13 is plastically deformed after the press working, whereby the marker insert is fitted and fixed to the opening 26 of the marker housing 14 by frictional engagement generated on a substantially whole interface between the marker insert 13 and the lumen surface 26a of the opening 26.

According to the production method of the present invention, it is difficult to form steps and gaps at the boundary between the marker insert 13 and the marker housing 14 and peripheral parts thereof, and thus a stent having an excellent corrosion resistance can be produced.

According to a conventional general production method as shown in FIG. 6, an indenter 61 whose proximal region 62 has a radius of $R_4$ and whose distal end is flat presses the marker insert 13 to pressure fit and fix the marker insert 13 to the marker housing 14. According to the method, however, the $R_4$ must be larger than a radius of the marker insert 13, and the indenter is brought into contact with the marker housing 14 during the press working, whereby the marker housing and the stent are deformed, and there is a tendency in which it is difficult to pressure fit the marker insert without forming steps or gaps.

In the indenter 21, which is used in the present invention, the shape of the proximal region 22 is not particularly limited within a range in which the effects of the present invention are not impaired. A cross-sectional shape of an area in a direction of the central axis 210, which area may be a part or may run the full length, orthogonal to the direction of the central axis 210, may include, for example, polygons such as a square and a rectangle, a circle, an ellipse, and the like. In particular, it is preferable that the cross-sectional shape of the area in the direction of the central axis 210, which area may be a part or may run the full length, on a side adjacent to the marker insert 13 in the proximal region 22 is a circle; in other words, a cylindrical or columnar proximal region is preferable, in terms of a easy processing of the distal end into a partially spherical surface, and the strength. A proximal region whose cross-sectional shape is cylindrical in the full length is more preferable. When the proximal region 22 is cylindrical-shaped or columnar-shaped, an outside diameter $D_1$ of the proximal region 22 can be appropriately selected according to the size of the opening 26 of the marker housing 14, or a radius of curvature $R_1$ of the partially spherical tip shape 23, and is preferably a size capable of providing a strength withstandable to the press working to the indenter 21. It is particularly preferable that the outside diameter $D_1$ is larger than the inside diameter $D_3$ of the opening 26 of the marker housing 14, because it is easy that the load is uniformly applied to the whole marker insert 13 to be fixed to the inside of the marker housing 14 during the press working, and it is easy to prevent the falling away.

In the indenter 21 used in the present invention, the radius of curvature $R_1$ of the partially spherical tip shape 23 can be appropriately selected considering the properties of the material from which the marker insert 13 is formed (the marker insert 13a which has not been pressed yet), the inside diameter $D_3$ of the opening 26 of the marker housing 14, and the like, and preferably have a size equal to or larger than a radius of the opening 26, i.e., equal to or larger than the ½ inside diameter $D_3$, because the load can be efficiently applied to the marker insert 13 without the contact of the indenter 21 with the outer surface 25 of the marker housing 14.

A material used in the indenter 21 is not particularly limited so long as it is a material which is not broken or plastically deformed during the press working, and stainless steels, carbon steels, cemented carbide, and the like can be preferably used.

The shape of the marker insert 13, which has not been pressed yet, is not particularly limited so long as it can be inserted into the opening 26 of the marker housing 14 and installed thereon, the recessed partially spherical surface can be formed by the press, and it can be closely brought into contact with the whole lumen wall surface of the opening 26. For example, when the marker insert is inserted into a columnar space such as the opening 26 in the present embodiment and installed thereon, the shape thereof may include a partially spherical shape, a rivet shape, a cylindrical shape, a convex lens shape, a truncated cone shape, and the like. Of these, the cylindrical shape is preferable, because it is easy to pressure fit it to the marker housing 14 to strongly fix it thereon.

The outside diameter $D_2$ of the marker insert 13, which has not been pressed yet, used in the present invention is not particularly limited so long as the visibility under an X-ray illumination can be secured, and is preferably within a range of 0.25 to 1.00 mm, in terms of the excellent visibility for the marker 12 under an X-ray illumination.

A thickness $T_2$ of the marker insert 13a, which has not been pressed yet, is not particularly limited so long as the marker insert can be fitted to the opening 26 without the contact of the indenter 21 with the surface of the marker housing 14 during the press working, and is preferably a thickness 0.02 to 0.10 mm larger than the depth $T_3$ of the opening 26 of the marker housing 14, because a movable distance in an up and down direction can be set long during the press working.

A volume of the marker insert 13a, which has not been pressed yet, is not particularly limited so long as the marker insert can be pressure fitted to the opening 26 and fixed it thereon by the press working without the contact of the indenter 21 with the outer surface 25 of the marker housing 14 during the press working.

A shape of the lumen in the opening 26 of the marker housing 14 used in the present invention is not particularly limited so long as the marker insert can be inserted thereto and installed thereon. The lumen may have a columnar or a truncated cone shape, or may be a non-through hole.

An inside diameter $D_3$ of the marker housing 14 (corresponding to an outside diameter of the opening 26) is preferably a size capable of easily introducing and installing the marker insert 13a, which has not been pressed yet, and causing no remarkable gap between the center of the opening 26 and the center of the marker insert 13a, which has not been pressed yet, during the press working. Specifically, the diameter is preferably a size 0.01 to 0.10 mm larger than the outside diameter $D_2$ of the marker insert 13a, which has not been pressed yet.

(Stent Production Device and Stent Production Method Using Same)
<Stent Production Device>

As for a stent production device and a stent production method using the same of the present invention, one embodiment thereof will be specifically explained below, referring to FIG. 8, but the stent production device and the stent production method using the same of the present invention are not limited thereto. Explanations will be made taking the stent shown in the development view, FIG. 1 (a), as an example, but it is also not limited thereto.

Figure 8:
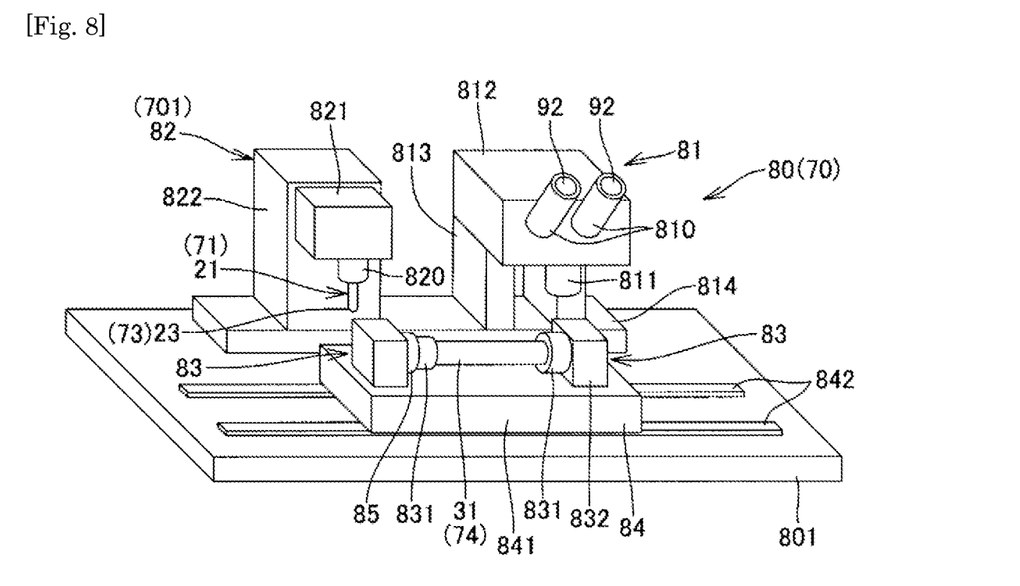
FIG. 8 is a perspective view showing a device for producing a stent of the present invention.

FIG. 8 is a perspective view schematically showing one embodiment of a stent production device of the present invention.

In the embodiment shown in FIG. 8, a stent production device 80 includes a mandrel 31, a microscope 81, a press apparatus 82, a mandrel-gripping mechanism 83, a mechanism 84 of moving a mandrel in an axial direction, and a mechanism 85 of rotating a mandrel. These parts are installed on a base 801.

The mandrel 31 is removable from the production device 80, and thus when a tubular body stent previously produced, on which the marker insert has not installed yet, (hereinafter referred to as a stent member), is installed on the production device 80, it is possible that the mandrel 31 is once removed from the production device 80, the mandrel 31 is inserted into the stent member, and then the mandrel 31 into which the stent member is inserted is installed and fixed on the production device 80.

The mandrel 31 has preferably an outside diameter equal to or larger than an inside diameter of the stent, for inserting and fixing the stent member. The upper limit of the outside diameter is preferably a diameter at which the mesh structure part of the stent does not plastically deform. In such a case, the outside diameter is generally preferably a size of an inside diameter of the stent member plus 1 mm, or less, more preferably, a size of the inside diameter plus 0.2 mm, or less, although it depends on the mesh shape. This is preferable because the stent member can be easily fixed on the mandrel and the relative displacement of the stent member to the mandrel can be inhibited utilizing the elasticity of the mesh structure. The mandrel may have a mechanism for fixing the stent member, for example, various chuck mechanisms including a mechanical chuck, a magnet chuck, a vacuum chuck, an air chuck, and the like, which are not shown in the drawing. When the mandrel has such a mechanism, the stent member can be easily fixed on the mandrel 31, even if the outside diameter of the mandrel 31 is smaller than the inside diameter of the stent.

A material which can be used for the mandrel 31 is not particularly limited, so long as it is not broken or plastically deformed during the press working. For example, stainless steels, carbon steels, cemented carbide, and the like can be preferably used.

The microscope 81 can be preferably used to confirm an arrangement state of the marker insert 13a before the press working and an arrangement state of the marker insert 13 after the press working in the inside of the opening 26 of the marker housing 14, and a state of the outer surface 25 of the marker housing 14, and the like. The microscope 81 is an optical microscope, particularly a stereoscopic microscope, and includes a lens-barrel part 812 having a binocular eye-piece part 810 and an object lens part 811, and a frame 814 having a microscope pillar part 813 movably supporting in an up and down direction the lens-barrel part 812. It is possible to move up and down the lens-barrel part 812 by using height-adjusting screws (not shown), or the like. In the present invention, an object lens used in the object lens part has preferably an optical magnification of 5 to 100×, in order to sufficiently confirm the states of the marker insert before and after the press.

Figure 9:
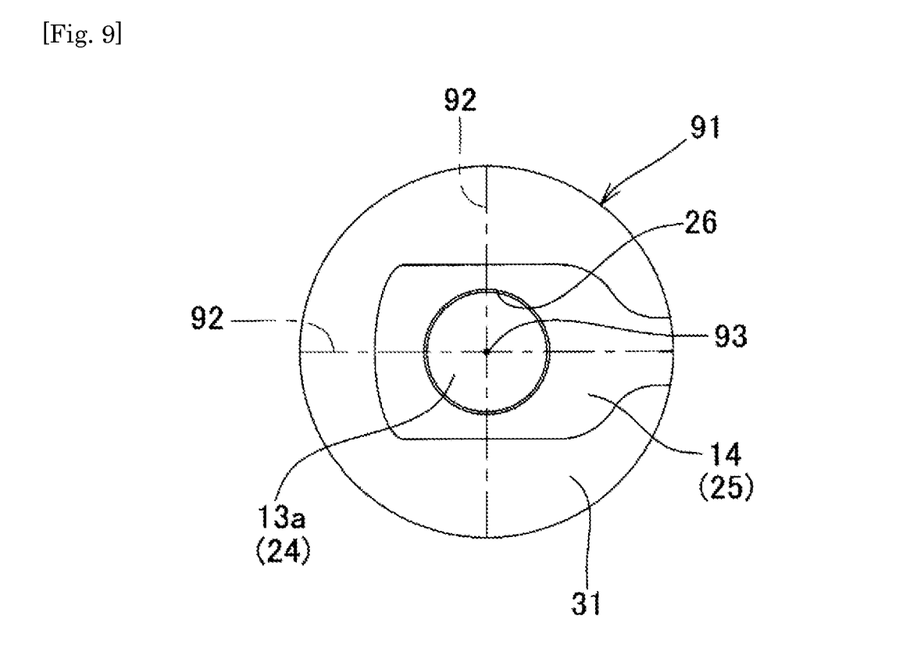
FIG. 9 is a schematic view showing a microscope visual field at the time of positioning of an insert arrangement of a marker insert before press working in a method for producing a stent of the present invention.

One of eye-pieces 91 used in the eye-piece part 810 of the microscope 81 preferably has multiple additional lines 92 whose intersection point is consistent with the center 93 of the visual field, which can be seen in a microscope visual field, as shown in FIG. 9. This makes an operation of positioning the marker insert 13a to the opening 26 easier, when, in the stent member through which the mandrel 31 is inserted, the marker insert 13a, which has not been pressed yet, is inserted into and installed on the opening 26 of the marker housing 14.

A commercially available one can be used as the microscope 81 as described above.

A light source for brightening the microscope visual field, which is not shown, may be provided.

The press apparatus 82 includes an indenter 21 for pressure fitting the marker insert 13 to the opening 26 provided on the marker housing 14 by pressing the marker insert 13a, which has not been pressed yet. The indenter 21, as described above, includes the proximal region 22 and the distal end 27, which are connected to each other in the direction of the central axis, the distal end 27 having a partially spherical shape (partially spherical tip shape 23) (see FIGS. 2 to 5). In the present embodiment, the indenter 21 is fixed on a movable part 820, which can be moved in a direction of the central axis thereof (hereinafter which may sometimes refer to as an up and down direction). The movable part 820 is supported by a supporting part 821, the supporting part 821 is fixed on a supporting pillar 822, and the supporting pillar 822 is fixed on the frame 814. It is preferable that a load cell (not shown) is attached to the movable part 820. When the load cell is attached, a load can be confirmed during the press working. It is preferable that the movable part 820 can be precisely moved in the up and down direction, whereby the press working can be performed more precisely.

In the movable part 820, the indenter 21 has preferably a detachable structure, because such a movable part can be applied to a marker housing having various sizes and shapes, or a stent member having such a marker housing.

It is preferable that the press apparatus 82 is connected to an electric device (not shown) for controlling and recording a moving speed and a moving distance of the movable part 820, a load generated by the indenter 21 fixed on the movable part 820 during the press working, and the like. When the electric device is used, press working conditions such as a press load, a moving speed, a moving displacement, and a holding time during the press pressurization can be set, executed, and recorded. Such a press apparatus can be realized, for example, by applying the indenter 21 described above to a desktop type compression tester provided with a load cell.

The shape and holding manner of the mandrel-gripping mechanism 83 are not particularly limited so long as the mechanism has a function of detachably holding and fixing both edges of the mandrel 31. It is preferable to form it from a chuck mechanism such as a mechanical chuck, a magnet chuck, an air chuck, or a vacuum chuck, in terms of easy attachment and detachment of the mandrel 31. It is possible that one edge of the mandrel 31 is partially inserted into an opening (not shown) formed on the mandrel-gripping mechanism 83, and the mandrel 31 is held and fixed by using, for example, the air chuck.

In the example shown in FIG. 8, a pair of mandrel-gripping mechanisms 83 are provided so that both edges of the mandrel 31 in a major axis direction thereof are held. Each mandrel-gripping mechanism 83 has a holding part 831, which holds one edge of the mandrel 31, and a supporting part 832, which supports the holding part 831. At least one of the holding parts 831 has the chuck mechanism described above. The other holding part 831, accordingly, may include only an opening (not shown), which receives the edge of the mandrel 31. It is also possible, in order to attach and detach the mandrel 31, that the supporting part 832 is made movable in a major axis direction of the mandrel 31 together with the holding part 831, the parts described above are made detachable from the moving mechanism 84, or the holding part 831 is made detachable from the supporting part 832, although they are not shown in the drawing.

The mechanism 85 of rotating a mandrel can integrally rotate the stent member, through which the mandrel 31 is inserted and on which it is fixed, with the mandrel 31 by rotating the mandrel 31 fixed by the holding part 831 of the mandrel-gripping mechanism 83 on the central axis in the major axis direction, whereby the marker housing 14, and the marker inserts 13a and 13 before and after the press can be precisely positioned, during the press working and the observation with the microscope. It is also preferable to have a function capable of rotating the holding part 831 of the mandrel-gripping mechanism 83 during the rotation of the mandrel 31. In the example shown in FIG. 8, the mechanism 85 of rotating a mandrel is supported on the supporting part 832 of one of the mandrel-gripping mechanisms 83 together with the holding part 831. In the mechanism 85 of rotating a mandrel, the mandrel 31 held on the holding part 831 is rotated by rotating the holding part 831. In the present example, the mechanism 85 of rotating a mandrel is provided only on one mandrel-gripping mechanism 83, but it may be provided on the both.

The mechanism 84 of moving a mandrel in an axial direction refers to a mechanism in which the mandrel can be relatively moved so that the central axis 210 of the indenter 21 is consistent with the center 93 of the visual field of the microscope; in other words, it refers to a mechanism in which the mandrel 31 can be moved relatively to the press apparatus 82 and the microscope 81 so that a pre-determined position of the mandrel 31 is consistent with the central axis 210 of the indenter 21 and the center 93 of the visual field of the microscope. The pre-determined position of the mandrel 31 refers to the center of the opening 26 of the marker housing 14 of the stent member into which the mandrel 31 is inserted. The center conceptionally includes vicinity parts thereof within a range in which desirable press working can be performed.

The mechanism capable of relatively moving refers to a mechanism in which the mandrel 31 is moved to the fixed press apparatus 82 and the microscope 81 so that the pre-determined position of the mandrel 31 is consistent with the central axis 210 of the indenter 21 in the press apparatus 82 and the center 93 of the visual field of the microscope; or a mechanism in which the press apparatus 82 and the microscope 81 are moved in a situation in which the mandrel 31 is fixed.

For example, the mechanism 84 of moving a mandrel in an axial direction shown in FIG. 8 is a mechanism in which a unit having the mandrel 31, the mandrel-gripping mechanism 83, and the mechanism 85 of rotating a mandrel put on a movable stand 841 is moved along a pair of parallel linear rails 842 fixed on the base 801, and the mandrel 31 is moved in an axial direction of the mandrel toward the press apparatus 82 fixed on the base 801 along the rails 842, and the microscope 81. The rails 842 may be curved so long as the mandrel 31 can be moved relatively to the press apparatus 82 and the microscope 81 so that the pre-determined position of the mandrel 31 is consistent with the central axis 210 of the indenter 21 and the center 93 of the visual field of the microscope, which is not illustrated in the drawing.

The mechanism 84 of moving a mandrel in an axial direction has preferably a stopper mechanism capable of stopping and fixing the mandrel at a position at which the pre-determined position of the mandrel 31 is consistent with the center 93 of the visual field of the microscope 81 and the central axis 210 of the indenter 21 in the press apparatus 82. The movable stand 841 may be manually moved or automatically moved using a driving device which is not shown in the drawing.

<Stent Production Method Using Stent Production Device of the Present Invention>

Next, a stent production method using a stent production device of the present invention will be explained, taking a case where the stent production device 80 shown in FIG. 8 is used as an example.

First, for example, a cylindrical stent member having a mesh structure part shown in FIG. 1(*a*) and a marker housing 14, but no marker insert 13 is produced.

Then, a mandrel 31 is inserted into the cylindrical stent member to fix the stent member on the mandrel 31. The mandrel 31 is fixed by a mandrel-gripping mechanism 83 (here, a mechanical chuck called as a drill chuck for fixing drills on a drilling machine).

At that time, a method of inserting the marker insert 13*a*, which has not been pressed yet, into an opening 26 of the marker housing 14 and installing the marker insert thereon is not particularly limited, and the marker insert 13*a*, which has not been pressed yet, may be held with tweezers to insert and install it, or it may be inserted and installed by using an automated device (not shown). The state in which the marker insert 13*a*, which has not been pressed yet, is installed on the opening 26 of the marker housing 14 can be observed and confirmed by using a microscope 81.

Next, as shown in FIG. 9, positioning is performed operating a mechanism 84 of moving a mandrel in an axial direction and/or a mechanism 85 of rotating a mandrel so that each intersection point of additional lines 92 (the center 93 of the visual field) is consistent with the center of the marker insert 13*a*, which has not been pressed yet. Then, the stent member is moved together with the mandrel 31 to a position at which the center of the marker insert 13*a*, which is positioned as the pre-determined position of the mandrel 31, is consistent with the central axis 210 of the indenter 21 on a side of the press apparatus 82, operating the mechanism 84 of moving a mandrel in an axial direction, whereby the central axis 210 of the indenter 21 is matched to the center of the marker insert 13*a*, which has not been pressed yet. The moving distance at that time is a minimum distance between the central axis 210 of the indenter 21 and a straight line which is parallel to the central axis 210 and passes through the center 93 of the microscope visual field. It is enough accordingly that the movable stand 841 is linearly moved along the rails 842 by the minimum distance.

The marker insert 13 can be pressure fitted to the marker housing 14 to fix the marker insert thereon by moving the indenter 21 in a direction of the central axis 210 thereof (for example, an up and down direction) using the press apparatus 82, and plastically deforming the marker insert 13*a*, which has not been pressed yet, by the press working. It is preferable that the press working is performed while a compressive load caused by pressing the marker insert 13*a* with the desired indenter 21, a holding time of the compressive load, a moving speed of the indenter 21, a moving displacement in a direction of the central axis 210 of the indenter 21, and the like are controlled by using an electrical device (not shown) connected to the press apparatus 82. The fixed state of the marker insert 13 after the fixing, and the state of the outer surface of the marker housing (i.e., the state of the marker 12) can be confirmed with the microscope 81 by moving again the stent 11 into which the mandrel 31 is inserted from the press apparatus 82 side to the microscope 81 side using the mechanism 84 of moving the mandrel. When the state of the marker 12 is confirmed in more detailed, the observation may be performed using an electronic microscope.

<Method of Evaluating Holding Strength of Marker Insert Utilizing Stent Production Device of the Present Invention>

According to a stent production device of the present invention, it is possible to evaluate a holding strength of a marker insert pressure fitted to and fixed on the opening of a marker housing by utilizing the same. One embodiment of the evaluation devices and evaluation methods utilizing a stent production device 80 shown in FIG. 8 will be explained below, referring to FIGS. 7 and 8.

<<Evaluation Device>>

An evaluation device is obtained by alternating the indenter 21 and the mandrel 31 in the stent production device 80 shown in FIG. 8 to structures suitable for an evaluation method. Explanations will be made below, accordingly, for the indenter and the mandrel in the evaluation device. The same numbers are applied to the common components in both of the stent production device 80 shown in FIG. 8 and the evaluation device, and explanations will be made referring to FIG. 8.

Figure 7:
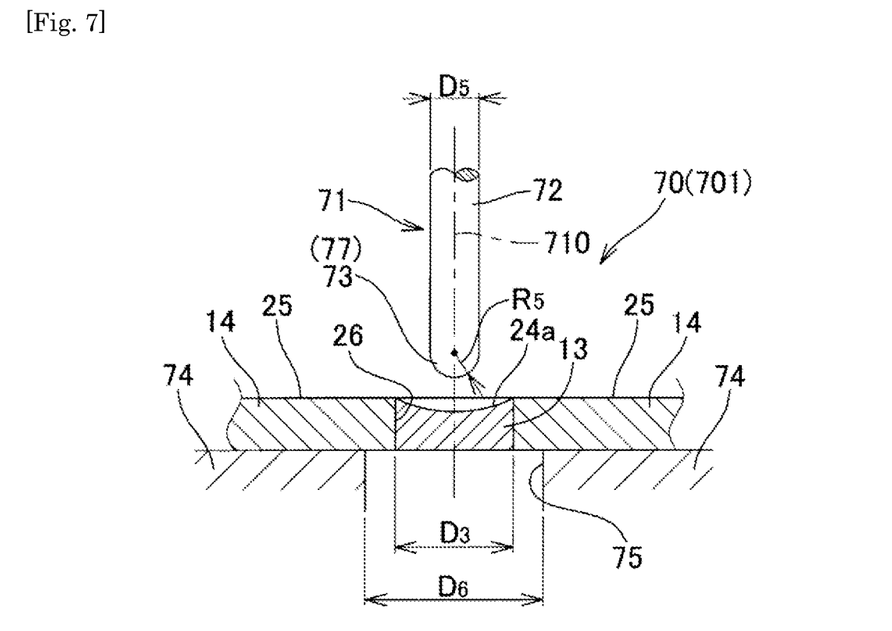
FIG. 7 is a cross-sectional view showing a method for evaluating a holding strength of a marker insert in the present invention.

FIG. 7 schematically shows a part of an indenter 71 mounted on a movable part 820 of a press apparatus 701 in an evaluation device 70 of the present embodiment, and partial cross-sections of a mandrel 74, and a marker insert 13 fixed on a marker housing 14 in a stent 11 into which the mandrel 74 is inserted, which is an explanation drawing for explaining the method of evaluating a holding strength.

The indenter 71 which is preferably used for the holding strength evaluation, is formed from a proximal region 72 and a distal end 77, which are continued to each other in a direction of a central axis 710 of the indenter 71, as the indenter 21 which is preferably used in the production method of the present invention. The distal end 77 has preferably a partially spherical shape. A number 73 is applied to the sphere-shaped distal end 77, which is referred to as a partially spherical tip shape, in the following explanations. The central axis 710 is consistent with a central axis 710 of the indenter 21 in the stent production device 80. The shape of the proximal region 72 in the indenter 71 is not particularly limited within a range in which the effects of the present invention are not impaired. A cross-sectional shape of an area in a direction of the central axis 710, which area may be a part or may run the full length, orthogonal to the direction of the central axis 210, may include, for example, polygons such as a square and a rectangle, a circle, an ellipse, and the like. Especially, the cross-sectional shape of the area, which area runs the full length, in the proximal region 72 is preferably a circle; in other words, a cylindrical or columnar proximal region is preferable, because transmission of a load can be efficiently performed without stress concentration to specific sites during the holding strength evaluation, thus resulting in precise evaluation.

When the proximal region 72 is cylindrical- or columnar-shaped, an outside diameter $D_5$ of the proximal region 72 can be appropriately selected according to a size of the opening 26 and a radius of curvature $R_5$ of the partially spherical tip shape 73. It is preferable to set the outside diameter $D_5$ of the proximal region 72 to a size smaller than an inside diameter $D_3$ of the opening 26 of the marker housing 14.

A mandrel 74, which can be preferably used for the holding strength evaluation, has the same shape and the same functions as in the mandrel which is preferably used in the production method of the present invention, except that it has an opening 75 on the surface thereof.

An inside diameter $D_6$ of the opening 75 formed on the surface of the mandrel 74 is preferably larger than the inside diameter $D_3$ of the opening 26 of the marker housing 14.

Materials used for the indenter 71 and mandrel 74 for the holding strength evaluation have preferably the same properties as those of the indenter 21 and the mandrel 31, which can be preferably used in the stent production method and the production device of the present invention, respectively.

<<Evaluation Method Using Evaluation Device>>

A method for evaluating a holding strength of a marker insert pressure fitted to and fixed on a marker housing, utilizing a stent production device of the present invention, will be explained below, taking a case where the evaluation device described above is used as an example.

A position of a marker insert 13 is decided, and the marker insert 13 is pressed using an indenter 71 in the same manner as in the case of <Stent production method using stent production device of the present invention> described above. Then, a holding strength of the marker insert 13 can be evaluated by measuring a load on the press. Explanations will be briefly made below.

First, a mandrel 74 is inserted into a stent 11 in which a marker insert 13 is fixed on an opening 26 of a marker housing 14, and the mandrel 74 is fixed by using a mandrel-gripping mechanism 83, while the state described above is maintained. Then, the positioning is performed using a mechanism 84 of moving a mandrel in an axial direction and/or a mechanism 85 of rotating a mandrel so that the center 93 of a visual field (see FIG. 9) is consistent with the center of the marker insert 13 and the whole marker insert 13 is located above an opening 75 of the mandrel 74 using an a microscope 81.

Next, a central axis 710 of the indenter 71 is matched to the center of the marker insert 13 by moving the stent 11, together with the mandrel 74, to a position at which the center of the marker insert 13 positioned as the pre-determined position of the mandrel 31 is consistent with the central axis 710 of the indenter 71 on a press apparatus 701 side operating the mechanism 84 of moving a mandrel in an axial direction.

Then, the indenter 71 is moved in a direction of the central axis 710 (an up and down direction) by using the press apparatus 701 until the marker insert 13 falls away from the opening 26 of the marker housing 14 to the opening 75 of the mandrel 74, and a holding strength at that time was measured, whereby the holding strength of the marker insert can be evaluated.

The holding strength can be evaluated from measurement results of press load values obtained from a time when the marker insert 13 comes into contact with the indenter 71 to a time when the marker insert 13 falls away. It is preferable for the press load value that the maximum value thereof is decided as a representative value, because the load reaches a peak just when the marker insert falls away.

As described above, the stent production method and the production device of the embodiments of the present invention have been specifically explained, but the present invention is not limited to the embodiments described above, and it is possible to implement the present invention adding modifications within a scope applicable to the gist described above and later, which are all encompassed within a technical scope of the present invention.

The production method and the production device of the present invention can be preferably applied to various stent having a marker insert, in addition to the stent exemplified, and the stent may include, for example, a balloon expandable stent, a stent-graft, and implantable medical devices such as a synthetic valve.

EXAMPLES

The present invention will be explained in more detailed referring to Examples and Comparative Examples.

In all of Examples and Comparative Examples described below, radiopaque markers were attached to a stent, and a holding strength evaluation was performed using a production device and an evaluation device of a stent shown in FIG. 8 or FIG. 9. Comparative Examples, however, are different from Examples in that an indenter shown in FIG. 6 was used, and an evaluation device used in the evaluation of the holding strength was different from the production device shown in FIG. 8 in that an indenter shown in FIG. 7 was used.

Example 1

A nickel-titanium alloy cylindrical stent member having an inside diameter of 8 mm, which, at each side thereof, had 4 marker housings 14 each provided with an opening having an inside diameter $D_3$ of 0.52 mm and a depth $T_3$ of 0.20 mm, and tantalum marker inserts 13a, which had not been pressed yet, having an outside diameter $D_2$ of 0.50 and a thickness $T_2$ of 0.23 mm were prepared.

A mandrel 31 having an outside diameter of 8 mm was inserted into a hollow part of a cylindrical stent 11, and the mandrel 31 was held by means of a mandrel-gripping mechanism 83. Then the marker insert 13 was fitted to the opening 26 of the marker housing 14, and adjustment was performed so that the center of the marker insert 13 is consistent with the center 93 of a microscope visual field using a microscope 81. After that, the mandrel 31 was moved by using a mechanism 84 of moving a mandrel in an axial direction so that the center of the marker insert 13, which is a pre-determined position of the mandrel 31, is consistent with the central axis 210 of an indenter 21.

The indenter 21 was moved at a speed of 10 mm/minute in a direction of the central axis 210 thereof by means of a movable part 820 in a press apparatus 82 including the indenter 21 having a proximal region 22 with an outside diameter $D_1$ of 1.00 mm and a partially spherical tip shape 23 with a radius of curvature $R_1$ of 0.50 mm as a distal end 27, and the marker insert 13a was pressed by the distal end 27 in the indenter 21 at a constant load of 100 N for 10 seconds to perform compression and deformation. After that, the load was removed therefrom; thus, the marker insert 13 was pressure fitted to and fixed in the marker housing 14. The operation described above was repeated 4 times to produce a stent having radiopaque markers (markers 1 to 4).

Example 2

A stent having radiopaque markers (markers 1 to 4) was produced in the same manner as in Example 1 except that an indenter 21 including an proximal region 22 with an outside diameter $D_1$ of 1.00 mm, and having a radius of curvature $R_1$ of 1.00 mm was used.

Example 3

A stent having radiopaque markers (markers 1 to 4) was produced in the same manner as in Example 1 except that the compression was performed at a constant load of 200 N for 10 seconds.

Comparative Example 1

A stent having radiopaque markers (markers 1 to 4) was produced in the same manner as in Example 1 except that an indenter 61 including a proximal region 62 with an outside diameter $D_4$ of 1.00 mm and a planar shape 63 with a radius $R_4$ of 0.50 mm at the tip was used.

Comparative Example 2

A stent having radiopaque markers (markers 1 to 4) was produced in the same manner as in Example 1 except that an indenter 61 including a proximal region 62 with an outside diameter $D_4$ of 2.00 mm and a planar shape 63 with a radius $R_4$ of 1.00 mm at the tip was used.

Comparative Example 3

A stent having radiopaque markers (markers 1 to 4) was produced in the same manner as in Example 3 except that an indenter 61 including a proximal region 62 with an outside diameter $D_4$ of 1.00 mm, and a planer shape 63 with a radius $R_4$ of 0.50 mm at the tip was used.

(Holding Strength of Marker)

Procedures of the evaluation of a holding strength of a marker will be shown below.

The stent produced in each Example or each Comparative Example was inserted into a mandrel 74 having an outside diameter of 8 mm, a marker part of the stent was fitted to and set in an opening 75 having an inside diameter $D_6$ of 0.60 mm on the surface of the mandrel 74, an indenter 71 including a proximal region 72 with an outside diameter $D_5$ of 0.20 mm and a partially spherical tip shape 73 with a radius of curvature $R_5$ of 0.15 mm at the tip was pushed at a speed of 10 mm/minute until the marker insert 13 fell away from the marker housing 14, and the maximum load measured at that time was evaluated as a holding strength of the marker. Evaluation results (the evaluation was performed in N=4) obtained in Examples and Comparative Examples are shown in Table 1. Table 1 shows, accordingly, measurement results of 4 markers 1 to 4 per stent from each Example or each Comparative Example.

(Appearance of Marker)

Procedures in the evaluation of appearance of a marker are shown below.

In the stent produced in each Example or each Comparative Example, the appearance of the outer surface of the marker housing 14 of the markers 1 to 4 was observed using a scanning electron microscope (S-3000N manufactured by Hitachi High-Tech Science Corporation). The observation of the marker housing 14 was evaluated in N=4, and the results are shown in Table 1. Table 1 shows, accordingly, measurement results of 4 markers 1 to 4 per stent from each Example or each Comparative Example.

One crack at one place in one sample among the four samples (a total: one place) in Comparative Example 2, and one crack at one place in four samples among the four samples (a total: four cracks) in Comparative Example 3 were confirmed. Cracks were not confirmed in Examples and Comparative Examples other than Comparative Example 2 and Comparative Example 3.

TABLE 1

| | Appearance of Marker (the number of cracks) | Holding Strength of Marker | | | | |
|---|---|---|---|---|---|---|
| | | Marker 1 | Marker 2 | Marker 3 | Marker 4 | Average Value |
| Example 1 | None | 13.8N | 14.1N | 15.4N | 13.6N | 14.3N |
| Example 2 | None | 14.4N | 13.5N | 14.4N | 15.9N | 14.6N |
| Example 3 | None | 15.4N | 14.5N | 14.4N | 14.9N | 14.8N |
| Comparative Example 1 | None | 5.2N | 4.8N | 6.2N | 4.5N | 5.2N |
| Comparative Example 2 | 1 | 3.2N | 3.8N | 4.2N | 4.8N | 4.0N |
| Comparative Example 3 | 4 | 11.8N | 10.2N | 9.2N | 10.4N | 10.4N |

(Results)

It is found that, in Examples 1 to 3, the holding strength of the marker insert is sufficiently large due to the effects of the present invention, and thus it is secured that the marker insert is difficult to fall away from the stent. In addition, it is found that there are no cracks on the marker housing 14 after the marker is attached thereto, and there is less influence of the stent on the marker housing due to the effect of the present invention.

It is found that, in Comparative Examples 1 and 2, the holding strength of the marker is low and it is not secured that the marker insert is difficult to fall away. In Comparative Example 2, the generation of cracks is confirmed on the marker housing 14 after the marker is attached thereto, and there are more than a few influences of the stent on the mesh structure part such as breakage of the stent during the use thereof. Why there is an influence of the sent on the mesh structure part when cracks are generated on the marker housing can be considered as follows: For example, when a stent is installed in an in vivo lumen, the stent receives a load of combined torsion, bending, compress, and the like due to pulsation, movement, and the like. If there are cracks on a marker housing, accordingly, the cracks are advanced to a mesh structure part, whereby the strength or the durability of the mesh structure part may be possibly reduced.

It is found that, in Comparative Example 3, the holding strength of the marker is relatively high, but the generation of cracks is confirmed on the marker housing 14 after the marker is attached thereto, and thus the efficient attachment of the marker is not performed.

From the above, it is found that the present invention is a method capable of inhibiting damages on the marker housing and the mesh structure part of the stent, and capable of efficiently performing the holding of the marker.

REFERENCE SIGNS LIST

11 Stent
12 Radiopaque marker (marker)
13 Marker insert
14 Marker housing
21 Indenter
22 Proximal region
23 Partially spherical tip shape
24 Marker insert outer surface
25 Marker housing outer surface 26 Opening
27 Distal end
31 Mandrel
61 Indenter
62 Proximal region
63 Planar tip shape
70 Evaluation device
71 Indenter
72 Proximal region
73 Partially spherical tip shape
74 Mandrel
75 Opening
80 Stent production device
81 Microscope
82 Press apparatus
83 Mandrel-gripping mechanism
84 Mechanism of moving mandrel in an axial direction
85 Mechanism of rotating mandrel
91 Eye-piece
92 Additional line
$D_1$ Outside diameter of proximal region
$R_1$ Radius of curvature of partially spherical tip shape
$D_2$ Outside diameter of marker insert
$T_2$ Thickness of marker insert
$D_3$ Inside diameter of marker housing opening
$T_3$ Depth of marker housing opening
$D_4$ Outside diameter of proximal region
$R_4$ Radius of planar tip shape
$D_5$ Outside diameter of proximal region
$R_5$ Radius of curvature of partially spherical tip shape
$D_6$ Inside diameter of opening

The invention claimed is:

1. A method for producing a stent which is formed into a tubular body and comprises at least one marker including a marker housing and a marker insert comprising:
    inserting the marker insert into an opening of the marker housing, the marker housing having a flat outer surface and the opening having an edge defined at the intersection with the flat outer surface;
    providing an indenter having a partially spherical shaped distal end; and
    pressing the marker insert by the indenter so that i) the partially spherical shaped distal end of the indenter comes into contact with an outer surface of the marker insert and does not come into contact with a surface of the flat outer surface of the marker housing at any moment, ii) the partially spherical shaped distal end of the indenter deforms the marker insert such that a recessed partially spherical shape is formed onto the outer surface of the marker insert, and iii) the marker insert is radially deformed to come into contact with a lumen surface of the opening of the marker housing and be pressure fitted to the opening of the marker housing to fix the marker insert to the marker housing, wherein
    the partially shaped distal end has a radius of curvature equal to or larger than an inside diameter of the opening of the marker housing, wherein
    the marker insert is deformed radially from a center of the outer surface of the marker insert as the marker insert is pressed by the partially spherical shaped distal end of the indenter,
    the partially spherical shaped distal end of the indenter pushes the marker insert more deeply than the outer surface of the marker housing toward the center of the outer surface of the marker insert, and
    the pressing of the marker insert by the indenter is stopped upon a height of periphery of the marker insert being at a same level with a height of the outer surface of the marker housing.

2. The method for producing the stent according to claim 1, wherein the indenter is formed of a proximal region and the partially spherical shaped distal end, the proximal region having a circular cross-sectional shape whose outside diameter is larger than an inside diameter of the opening of the marker housing.

3. The method for producing the stent according to claim 1 or 2, wherein the partially spherical shaped distal end has a radius of curvature larger than an inside diameter of the opening of the marker housing.

4. The method for producing the stent according to claim 1, further comprising matching a center of the marker insert to a central axis of the indenter.

5. The method for producing the stent according to claim 1, wherein the indenter allows load to be uniformly applied to a whole of the marker insert.

6. The method for producing the stent according to claim 1, wherein a lumen of the opening of the marker housing has a columnar shape or a truncated cone shape.

7. The method for producing the stent according to claim 1, wherein the marker insert has a columnar shape having a diameter $D_2$ and a height $T_2$,
    the opening of the marker housing has an inner diameter $D_3$ and a height $T_3$,
    $T_2$ is larger than $T_3$ by 0.03 mm to 0.10 mm, and
    $D_3$ is larger than $D_2$ by 0.01 mm to 0.10 mm.

8. The method for producing the stent according to claim 1, wherein the marker insert comprises tantalum, and
    the marker housing comprises nickel-titanium alloy.

9. A method for producing a stent which is formed into a tubular body and comprises at least one marker including a marker housing and a marker insert comprising:
    inserting the marker insert into an opening of the marker housing, the marker housing having a flat outer surface and the opening having an edge defined at the intersection with the flat outer surface;
    providing an indenter having a partially spherical shaped distal end; and
    pressing the marker insert by the indenter so that i) the partially spherical shaped distal end of the indenter comes into contact with an outer surface of the marker insert and said edge of the opening, but does not come into contact with a surface of the flat outer surface of the marker housing at any moment, except in contact with said edge of the opening, ii) the partially spherical shaped distal end of the indenter deforms the marker insert such that a recessed partially spherical shape is formed onto the outer surface of the marker insert, and iii) the marker insert is radially deformed to come into contact with a lumen surface of the opening of the marker housing and be pressure fitted to the opening of the marker housing to fix the marker insert to the marker housing, wherein
    the partially shaped distal end has a radius of curvature equal to or larger than an inside diameter of the opening of the marker housing,
    the marker insert is deformed radially from a center of the outer surface of the marker insert as the marker insert is pressed by the partially spherical shaped distal end of the indenter,
    the partially spherical shaped distal end of the indenter pushes the marker insert more deeply than the outer surface of the marker housing toward the center of the outer surface of the marker insert, and the pressing of the marker insert by the indenter is stopped upon a height of periphery of the marker insert being at a same level with a height of the outer surface of the marker housing.

* * * * *